US008100888B2

(12) United States Patent
Segawa et al.

(10) Patent No.: US 8,100,888 B2
(45) Date of Patent: Jan. 24, 2012

(54) CAPSULATED MEDICAL EQUIPMENT

(75) Inventors: Hidetake Segawa, Hachioji (JP);
Hironobu Takizawa, Hachioji (JP);
Hideyuki Adachi, Sagamihara (JP);
Takeshi Yokoi, Hino (JP)

(73) Assignee: Olympus Corporation, Tokyo (JP)

( * ) Notice: Subject to any disclaimer, the term of this patent is extended or adjusted under 35 U.S.C. 154(b) by 1310 days.

(21) Appl. No.: 11/436,787

(22) Filed: May 18, 2006

(65) Prior Publication Data
US 2006/0224063 A1    Oct. 5, 2006

Related U.S. Application Data

(63) Continuation of application No. 10/134,009, filed on Apr. 26, 2002, now Pat. No. 7,076,284.

(30) Foreign Application Priority Data

Oct. 16, 2001    (JP) .................................. 2001-318436

(51) Int. Cl.
*A61K 9/22*    (2006.01)
*A61B 1/00*    (2006.01)
(52) U.S. Cl. ..................................... 604/890.1; 600/117
(58) Field of Classification Search .................. 600/587, 600/117, 424, 431, 432
See application file for complete search history.

(56) References Cited

U.S. PATENT DOCUMENTS

| 3,683,389 | A | | 8/1972 | Hollis |
| 4,425,117 | A | * | 1/1984 | Hugemann et al. ........... 604/244 |
| 5,604,531 | A | | 2/1997 | Iddan et al. |
| 5,681,260 | A | | 10/1997 | Ueda et al. |
| 5,845,646 | A | * | 12/1998 | Lemelson ..................... 128/899 |
| 5,846,567 | A | * | 12/1998 | Kalloo et al. ................. 424/616 |
| 6,233,476 | B1 | | 5/2001 | Strommer et al. |
| 6,442,413 | B1 | | 8/2002 | Silver |
| 6,944,316 | B2 | | 9/2005 | Glukhovsky et al. |
| 7,039,453 | B2 | * | 5/2006 | Mullick et al. ................ 600/476 |
| 2002/0042562 | A1 | | 4/2002 | Meron et al. |
| 2002/0171669 | A1 | | 11/2002 | Meron et al. |
| 2002/0177779 | A1 | | 11/2002 | Adler et al. |
| 2002/0198470 | A1 | * | 12/2002 | Imran et al. ................... 600/587 |
| 2003/0028078 | A1 | | 2/2003 | Glukhovsky |
| 2003/0043263 | A1 | | 3/2003 | Glukhovsky et al. |
| 2004/0133089 | A1 | | 7/2004 | Kilcoyne et al. |

FOREIGN PATENT DOCUMENTS

| JP | 57-45833 | 3/1982 |
| JP | 4-8343 | 1/1992 |
| JP | 4-109927 | 4/1992 |
| JP | 4-144533 | 5/1992 |
| JP | 06-142081 | 5/1994 |
| JP | 6-285044 | 10/1994 |
| JP | 07-111985 | 5/1995 |
| JP | 09-065200 | 3/1997 |

(Continued)

*Primary Examiner* — Nicholas Lucchesi
*Assistant Examiner* — Jenna Zhang
(74) *Attorney, Agent, or Firm* — Scully, Scott, Murphy & Presser, P.C.

(57) ABSTRACT

A capsulated body having a facility, which acquires biomedical information through endoscopic examination or the like, incorporated therein is inserted into a duct within a living body. Whether the capsulated body has halted for a certain period of time is detected from the time-varying position of the capsulated body or a time-passing change in an image. If it is judged that the capsulated body has halted at a stenosed region or the like, the fact is notified so that the capsulated body can be collected immediately.

7 Claims, 13 Drawing Sheets

FOREIGN PATENT DOCUMENTS

| | | |
|---|---|---|
| JP | 2001-91860 | 4/2001 |
| JP | 2001-095756 | 4/2001 |
| JP | 2005-507687 | 3/2005 |
| WO | WO 92/21307 | 12/1992 |
| WO | WO 99/30610 | 6/1999 |
| WO | WO 00/22975 | 4/2000 |
| WO | WO 01/87377 A2 | 11/2001 |
| WO | WO 02/45567 A2 | 6/2002 |
| WO | WO 02/055126 A2 | 7/2002 |
| WO | WO 02/073507 A2 | 9/2002 |
| WO | WO 02/102223 A2 | 12/2002 |
| WO | WO 03/005877 A2 | 1/2003 |
| WO | WO 03/010967 A1 | 2/2003 |
| WO | WO 03/028224 | 4/2003 |

* cited by examiner

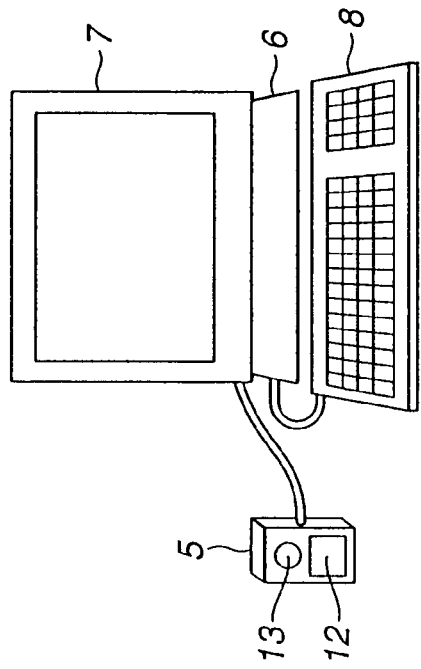
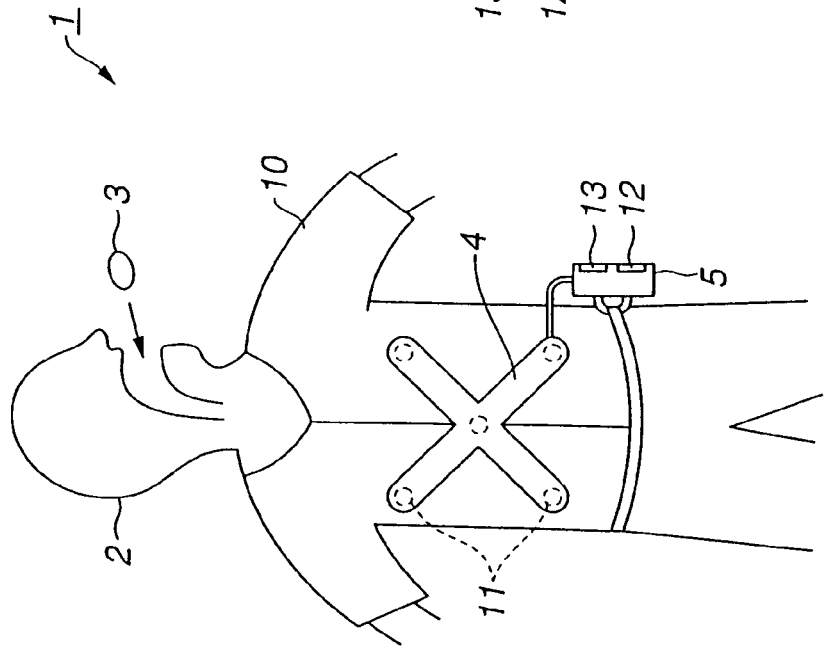

CAPSULATED MEDICAL EQUIPMENT

The present application is a continuation of U.S. patent application Ser. No. 10/134,009 filed Apr. 26, 2002, now U.S. Pat. No. 7,076,284 which claims the benefits of Japanese Application No. 2001-318436 which was filed on Oct. 16, 2001 and the contents of each of which are incorporated by reference.

BACKGROUND OF THE INVENTION

1. Field of the Invention

The present invention relates to capsulated medical equipment that is shaped like a capsule and that moves within a body cavity to perform examination or the like.

2. Description of the Related Art

In recent years, endoscopes and other medical equipment have been proposed for examining an intracavitary region or the like. Moreover, ordinary endoscopes are such that an insertion unit alone is inserted into a body cavity in order to perform endoscopic examination or the like. Medical equipment including a capsulated body that is shaped like a capsule and inserted into a body cavity in order to perform examination or the like has been disclosed in, for example, Japanese Unexamined Patent Application Publication No. 2001-91860.

In this type of capsulated medical equipment, the capsulated body may presumably be clogged at a stenosed region within a body cavity. If the capsulated body is clogged, it must be collected as soon as possible.

However, the related art described in the foregoing publication has not disclosed a countermeasure permitting early-stage detection of the clogged state of the capsulated body.

Moreover, a publication No. WO99/30610 of an unexamined international application under PCT discloses a related art that detects whether the acceleration in an axial direction is equal to or smaller than a predetermined value. If the acceleration is equal to or small than the predetermined value, a powering unit is disconnected for fear redundant image data may be acquired.

The above related art does not detect the clogged state of the capsulated body.

SUMMARY OF THE INVENTION

An object of the present invention is to provide capsulated medical equipment making it possible to detect whether a capsulated body is clogged at a stenosed region in a body cavity.

Another object of the present invention is to provide capsulated medical equipment making it possible to take appropriate measures in an early stage in case a capsulated body is clogged at a stenosed region in a body cavity.

Capsulated medical equipment in accordance with the present invention consists mainly of a capsulated body and a sensor unit. The capsulated body is inserted into a living body and passed through a duct within the living body, and includes a biomedical information detection unit that detects at least biomedical information. The sensor unit senses whether the capsulated body has halted in the duct within the living body for a certain period of time. If the capsulated body has halted in the duct within the living body, the state is sensed and the capsulated body is immediately collected or any other measures are taken immediately.

BRIEF DESCRIPTION OF THE DRAWINGS

FIG. 1A to FIG. 9 are concerned with the first embodiment of the present invention;

FIG. 1A shows the configuration of a capsulated endoscope system that is the first embodiment of capsulated medical equipment in accordance with the present invention in a practical state;

FIG. 1B shows a personal computer that is connected to an extracorporeal unit and that presents images or the like;

FIG. 3 is a block diagram showing the configuration of the extracorporeal unit;

FIG. 4 is an explanatory diagram concerning the principles of position calculation to be performed by a position calculation circuit;

FIG. 5 is a flowchart describing the actions to be performed by the first embodiment;

FIG. 6 is a block diagram showing the configuration of an extracorporeal unit included in a variant;

FIG. 7 is a flowchart describing the actions to be performed by the variant;

FIG. 8 is an explanatory diagram concerning a facility for detecting a fluid leakage;

FIG. 9 shows a capsulated endoscope included in a variant;

FIG. 10 schematically shows the configuration of an encapsulated endoscope in accordance with the second embodiment of the present invention;

FIG. 11 shows part of the internal configuration in a used state;

FIG. 12 is a flowchart describing the actions to be performed by the second embodiment;

FIG. 13 to FIG. 14C are concerned with the third embodiment of the present invention;

FIG. 13 shows the configuration of a capsulated endoscope system in which the third embodiment of the present invention is implemented;

FIG. 14A to FIG. 14C are a longitudinal sectional view of the flank of a capsulated endoscope, a sectional view of the face thereof that corresponds to the left-hand side of the longitudinal sectional view, and a sectional view of the back thereof that corresponds to the right-hand side of the longitudinal sectional view;

FIG. 15 shows the configuration of a main unit of capsulated medical equipment in accordance with the fourth embodiment of the present invention;

FIG. 16 shows the configuration of a main unit of capsulated medical equipment in accordance with the first variant; and FIG. 17 shows the configuration of a main unit of capsulated medical equipment in accordance with the second variant.

DESCRIPTION OF THE PREFERRED EMBODIMENTS

First Embodiment

Figure 2A:
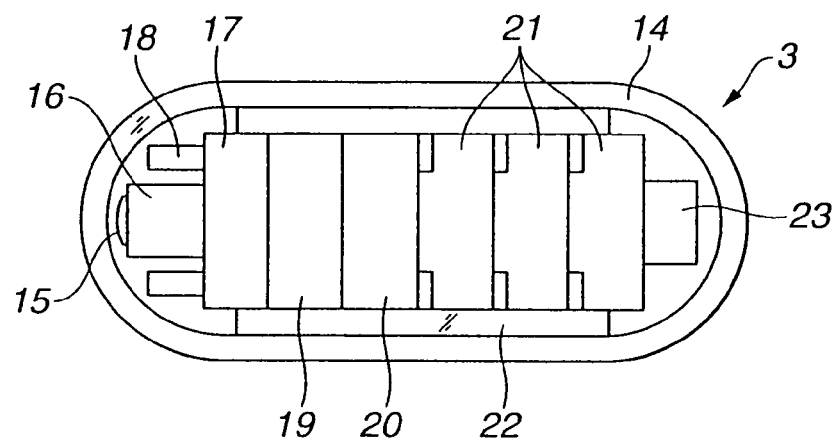
FIG. 2A shows the internal configuration of an encapsulated endoscope.

Referring to FIG. 1A to FIG. 9, the first embodiment of the present invention will be described below.

As shown in FIG. 1A, a capsulated endoscope system 1 in accordance with the first embodiment of the present invention consists mainly of a capsulated endoscope 3 (that is a capsulated body) and an extracorporeal unit 5 (placed away from the patient 2). The capsulated endoscope 3 is gulped down through the mouth of a patient 2, and transmits by radio an image signal that represents an optical image of the inner wall of an intracavitary duct while passing through the intracavitary duct. The extracorporeal unit 5 receives the signal sent from the capsulated endoscope 3 through an antenna unit 4 mounted on the extracorporeal region of the patient 2, and has a facility that preserves images.

As shown in FIG. 1B, the extracorporeal unit 5 is connected to a personal computer 6 so that it can be disconnected freely. The personal computer 6 fetches an image preserved in the extracorporeal unit 5, saves the image in an internal hard disk thereof, or displays the preserved image on a display device 7. A keyboard 8 to be used to enter data is connected to the personal computer 6.

As shown in FIG. 1A, when endoscopic examination is performed with the capsulated endoscope 3 gulped down, the antenna unit 4 composed of a plurality of antennas 11 is mounted on a garment 10 that is worn by the patient 2. The capsulated endoscope 3 images an intracavitary region. The antenna unit 4 receives a signal transmitted through an antenna incorporated in the capsulated endoscope 3. A picked up image is then preserved in the extracorporeal unit connected to the antenna unit 4. The extracorporeal unit 5 is mounted on, for example, a belt worn by the patient 2 using a freely detachable hook.

The extracorporeal unit 5 is shaped like, for example, a box. A liquid crystal monitor 12 that presents an image and a buzzer 13 that sounds a warning are mounted on the face of the extracorporeal unit 5.

As shown in FIG. 2A, the capsulated endoscope 3 is kept watertight while being encapsulated in a transparent armor member 14 that is shaped like a cylinder whose both end portions are rounded substantially like a hemisphere and blocked, that is, shaped like a capsule. Within the transparent armor member 14, an objective 15 that forms an image of an object is located in the middle of one end portion that is an imaging side while being enclosed in a lens frame 16. A solid-state imaging device, for example, a CMOS imager 17 is located at the position of the image plane of the objective 15.

Moreover, white light-emitting diodes (hereinafter white LEDs) 18 that glow in white are placed as an illumination system around the objective 15.

Moreover, for example, a control circuit (or processing circuit) 19, a communication circuit 20, and button-shaped batteries 21 are located behind the CMOS imager 17 while being placed inside a transparent cylindrical member 22 enclosed in the armor member 14. The control circuit 19 drives the white LEDs 18 so as to cause the white LEDs 18 to glow. Moreover, the control circuit 19 drives the CMOS imager 17 so as to produce an image signal representing an image picked up by the CMOS imager 17. The communication circuit 20 modulates the image signal to produce a signal to be transmitted. The button-shaped batteries 21 supply power to the circuits 19 and 20. An antenna 23 through which the image signal is transmitted by radio and which is connected to the communication circuit 20 is located behind the button-shaped batteries 21, that is, placed in the other hemispheric end portion.

Figure 2B:
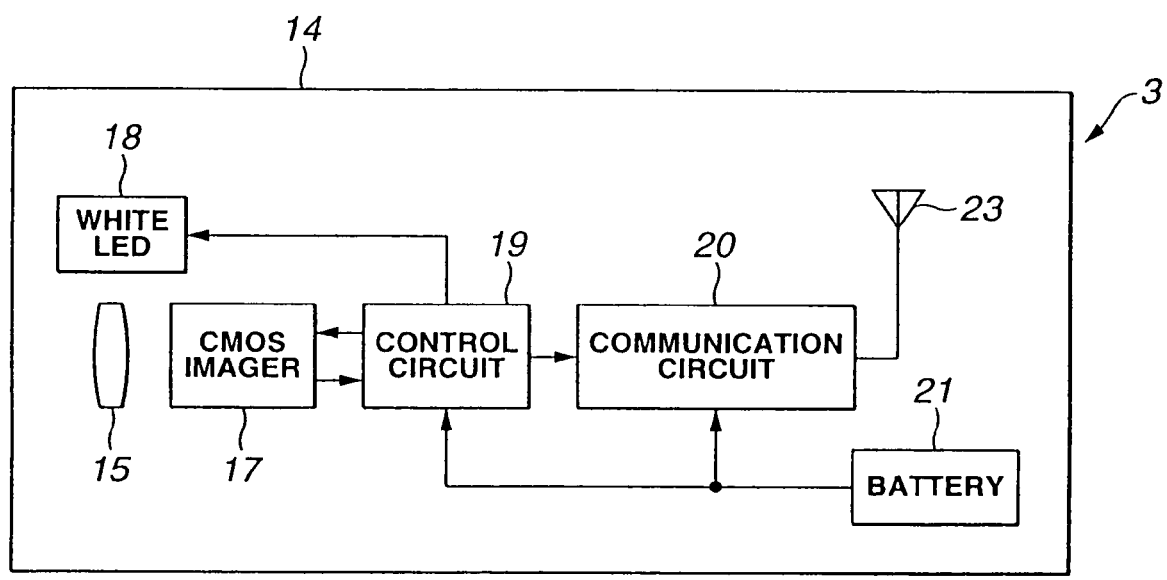
FIG. 2B is a block diagram showing the electrical configuration of the encapsulated endoscope.

FIG. 2B shows the electrical configuration of the capsulated endoscope 3 shown in FIG. 2A. The control circuit 19 that acts in receipt of power supplied from the batteries 21 allows the white LEDs 18 to glow. The white illumination light is then emitted from the face of the capsulated endoscope 3, whereby the inside of a body cavity through which the capsulated endoscope 3 passes is illuminated.

An image of an illuminated region is formed by the objective 15 adjoining the white LEDs 18, picked up by the CMOS imager 17, and photoelectrically transformed. In response to a driving signal sent from the control circuit 19, the CMOS imager 17 transfers an electric signal resulting from photoelectric transform to the control circuit 19. Consequently, an image signal is produced. The communication circuit 20 that acts in receipt of power supplied from the batteries 21 modulates the image signal. The resultant image signal is transmitted in the form of a radio wave to outside through the antenna 23.

Figure 3:
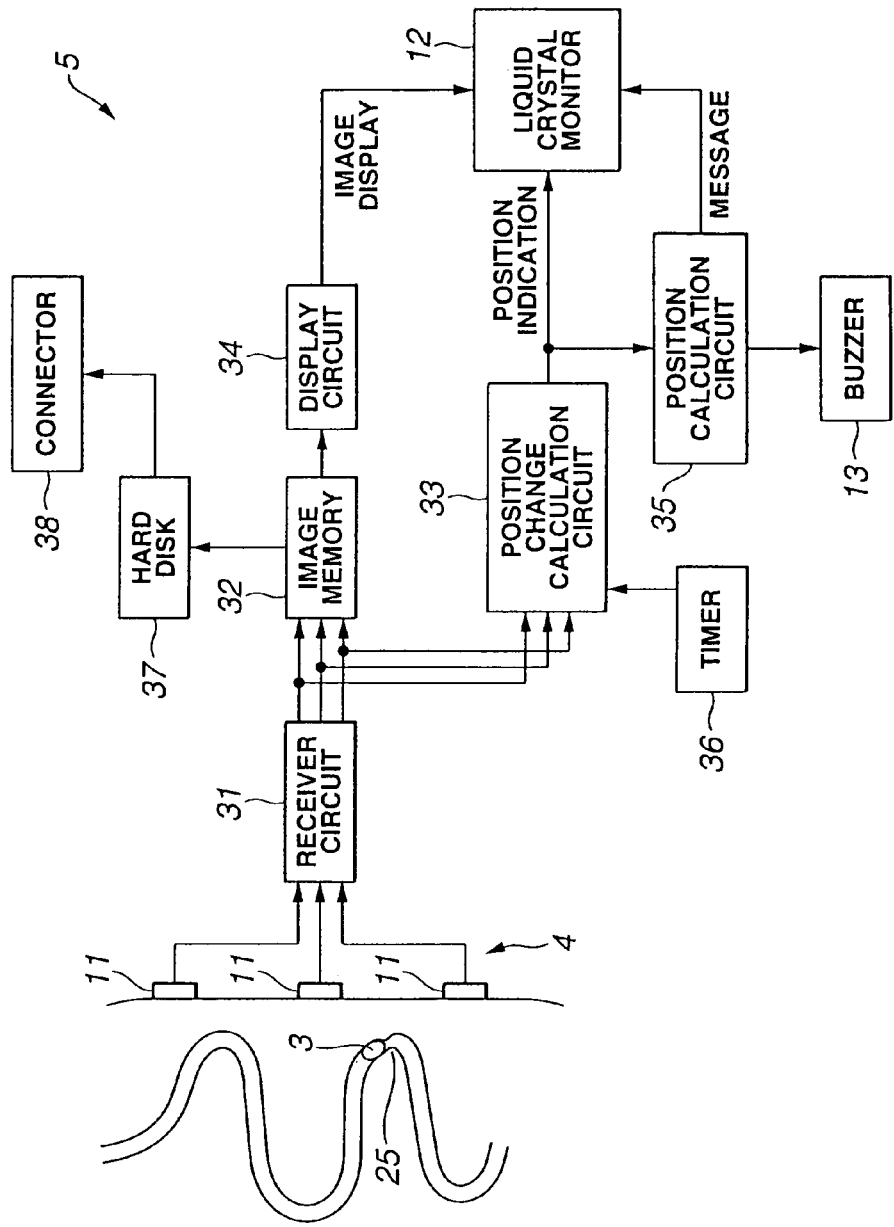

As shown in FIG. 3, when the capsulated endoscope 3 is used to perform endoscopic examination within, for example, the bowel, the extracorporeal unit 5 detects whether the capsulated endoscope 3 is clogged at a stenosed region 25. If the clogged state is detected, a warning is given.

The antennas 11 constituting the antenna unit 4 are connected to a receiver circuit 31 incorporated in the extracorporeal unit 5. Image data caught by the antennas 11, demodulated by the receiver circuit 31, and digitized is stored in an image memory 32, and transferred to a position calculation circuit 33. The position calculation circuit 33 is connected to a timer circuit 36 that is a timing means. A time instant at which image data is received can be referenced (measured).

The image data stored in the image memory 32 is processed in order to display an image via a display circuit 34. Consequently, a picked up image is displayed on the liquid crystal monitor 12.

Moreover, the position calculation circuit 33 calculates a three-dimensional position of the capsulated endoscope 3 by utilizing the strength of a signal transferred from the receiver circuit 31. The position calculation circuit 33 transfers position information to the liquid crystal monitor 12 so as to indicate the position, and also transfers the position information to a position change calculation circuit 35.

The position change calculation circuit 35 judges from position information sent from the position calculation circuit whether there is a time-passing change in the position of the capsulated endoscope 3. If it is judged that the position has not changed, it is judged that the capsulated endoscope 3 has halted at the stenosed region 25. A warning message is displayed on the liquid crystal monitor 12, and a buzzer 13 is sounded in order to give a warning.

The image memory 32 is connected to a hard disk 37. Image data provided as a signal having the largest amplitude among all image data items stored in the image memory 32 is preserved in the hard disk 37. The personal computer 6 is connected to the hard disk 37 via a connector 38, and reads image data from the hard disk 37 via the connector 38, and displays an image on the display device 7.

Figure 4:
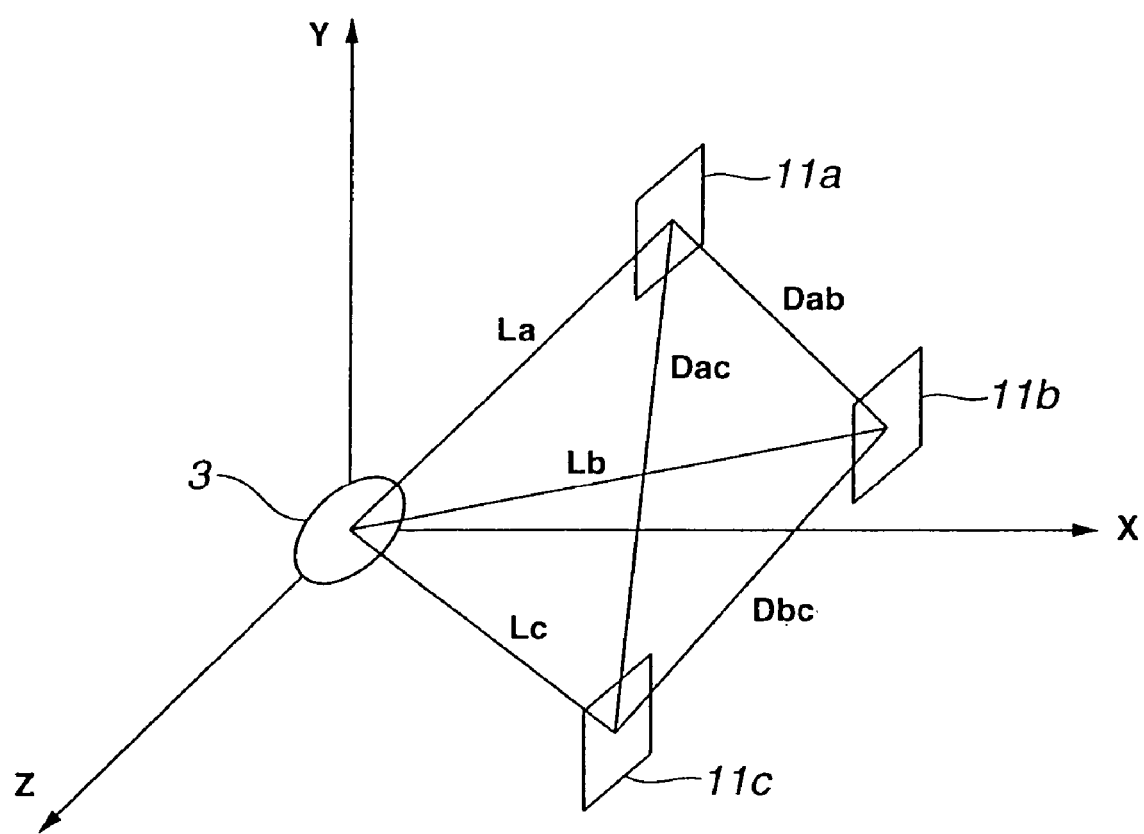

FIG. 4 is an explanatory diagram concerning the principles of position calculation to be performed by the position calculation circuit 33. FIG. 4 shows the relationships of the capsulated endoscope 3 to the antennas constituting the antenna unit 4 with the capsulated endoscope 3 located at an origin of three coordinate axes X, Y, and Z defined in a three-dimensional space.

A plurality of antennas constituting the antenna unit 4, or for brevity's sake, three antennas 11*a*, 11*b*, and 11*c* are located at known positions. Distances among the antennas are already known.

In the case shown in FIG. 4, the distances among the antennas include the distance Dab between the antennas 11*a* and 11*b*, the distance Dbc between the antennas 11*b* and 11*c*, and the distance Dac between the antennas 11*a* and 11*c*.

A signal of certain strength is delivered in the form of a radio wave from the antenna 23 incorporated in the capsulated endoscope 3. The strengths of signals caught by the antennas 11*i* (where i denotes a, b, or c) are provided as functions of the distances Li from (the antenna 23 incorporated in) the capsulated endoscope 3.

Therefore, the position calculation circuit 33 detects the strengths of signals received through the antennas 11*i* and calculates the distances Li to the (antenna 23 incorporated in) the capsulated endoscope 3.

Figure 5:
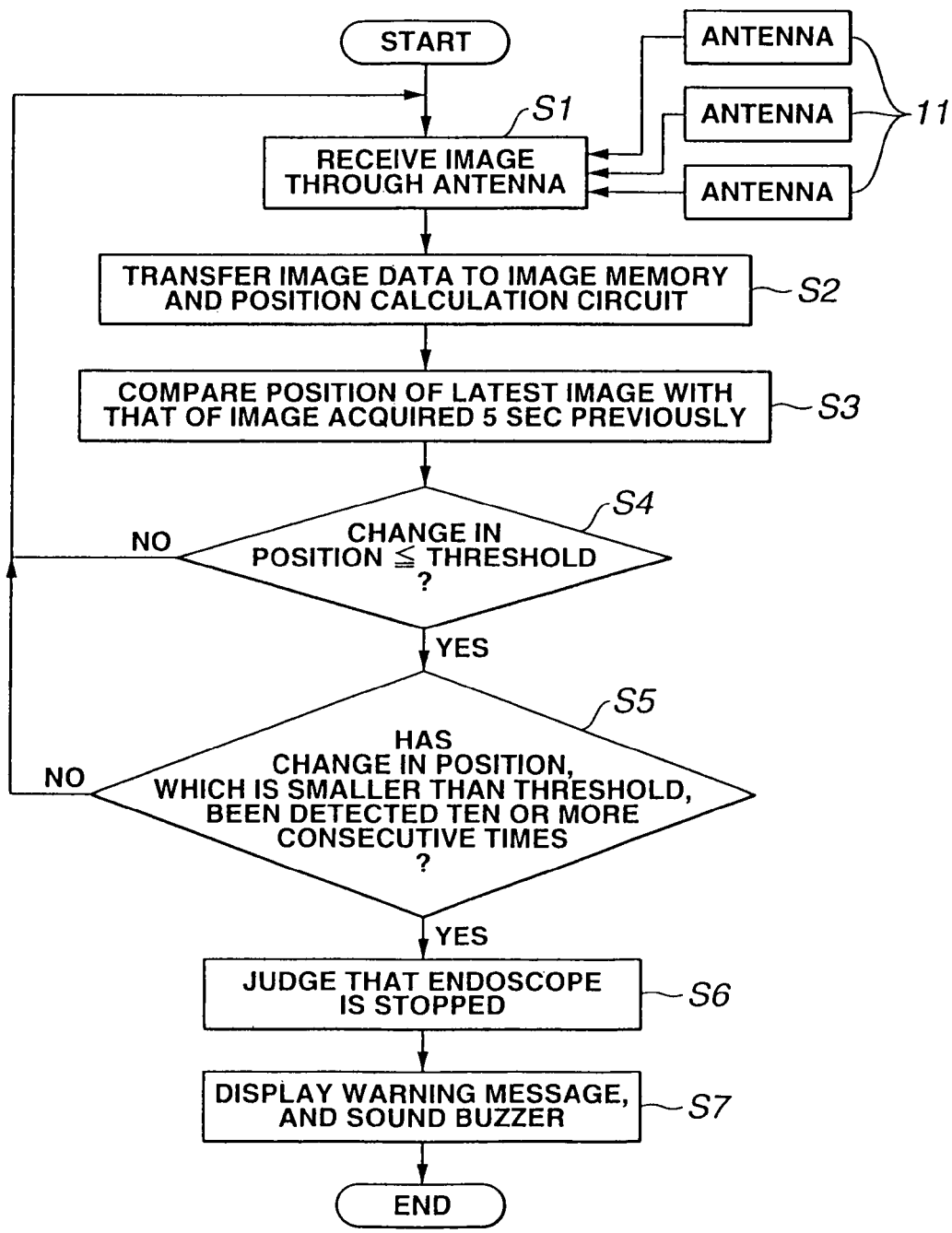

FIG. 5 is a flowchart describing a sequence of actions to be performed for giving a warning in case the capsulated endoscope 3 is clogged at the stenosed region 25 shown in FIG. 3.

When the sequence is started, the capsulated endoscope 3 illuminates and images an intracavitary region in short cycles, for example, at intervals (in cycles) of 0.5 sec. A picked up image is manipulated by the control circuit 19 and communication circuit 20 and radiated in the form of a radio wave at intervals of 0.5 sec to outside through the antenna 23.

The radio wave is received through the antennas 11 constituting the antenna unit 4 at step S1, whereby an image is received by the extracorporeal unit 5. Specifically, the receiver circuit 31 incorporated in the extracorporeal unit 5 receives the radio wave through the antennas 11 constituting the antenna unit 4 and demodulates it. At step S2, the image is then stored in the image memory 32 and transferred to the position calculation circuit 33.

The position calculation circuit 33 performs position calculation, and transmits position information together with time information provided by the timer circuit 36 to the position change calculation circuit 35. The position change calculation circuit 35 compares positions, which are detected for an appropriately short period of time, with each other using the time information and position information. To be more specific, at step S3, a position at which the capsulated endoscope 3 picks up the latest image is compared with a position at which the capsulated endoscope 3 has picked up an image 5 sec previously. Incidentally, the timer circuit 36 may transmit the time information directly to the position change calculation circuit 35.

The position change calculation circuit 35 judges from the result of position comparison whether the change in the position of the capsulated endoscope 3 is equal to or smaller than a pre-set threshold. (step S4).

If it is judged that the change in the position of the capsulated endoscope 3 is larger than the threshold, it is judged that the capsulated endoscope 3 has moved. Control is then returned to step S1. The processing from step S1 to step S4 is then repeated. If the change in the position is equal to or smaller than the threshold, the position change calculation circuit 35 judges whether the change in the position equal to or smaller than the threshold has been detected a set number of times, for example, ten or more consecutive times.

If it is judged that the above condition is not met, it is judged that the endoscope has not halted. Control is then returned to step S1, and the processing from step S1 to step S5 is repeated. In contrast, if the condition is met, that is, if the change in the position equal to or smaller than the threshold has been detected, for example, ten or more consecutive times, it is judged at step S6 that the endoscope has halted. At step S7, a warning action is performed based on the judgment of the halted state.

To be more specific, a message saying that the endo scope has halted is displayed on the liquid crystal monitor 12, and the buzzer 13 is sounded in order to give a warning. In this case, a staff member of an endoscopic laboratory takes measures immediately. That is to say, the staff member may insert, for example, an elongated endoscope through the mouth of the patient 2 so as to collect the capsulated endoscope 3. Otherwise, the staff member may dilate the stenosed region 25 so as to allow the capsulated endoscope 3 to pass it.

As mentioned above, the present embodiment includes a detecting means for detecting whether the capsulated endoscope 3 has halted for a predetermined period of time. If the capsulated endoscope 3 has halted at the stenosed region 25 or the like, the state can be recognized immediately because it is notified with a message displayed. Moreover, measures can be taken immediately in order to overcome the state.

In addition to the display of the warning message on the liquid crystal monitor 12 and the sounding of the buzzer, an LED may be lit or flickered in order to give a warning (notification).

Moreover, if the capsulated endoscope 3 is clogged at the stenosed region 25, a permanent magnet 61 or the like shown in FIG. 14A concerning the third embodiment that will be described later may be incorporated in order to overcome the clogged state.

Figure 6:
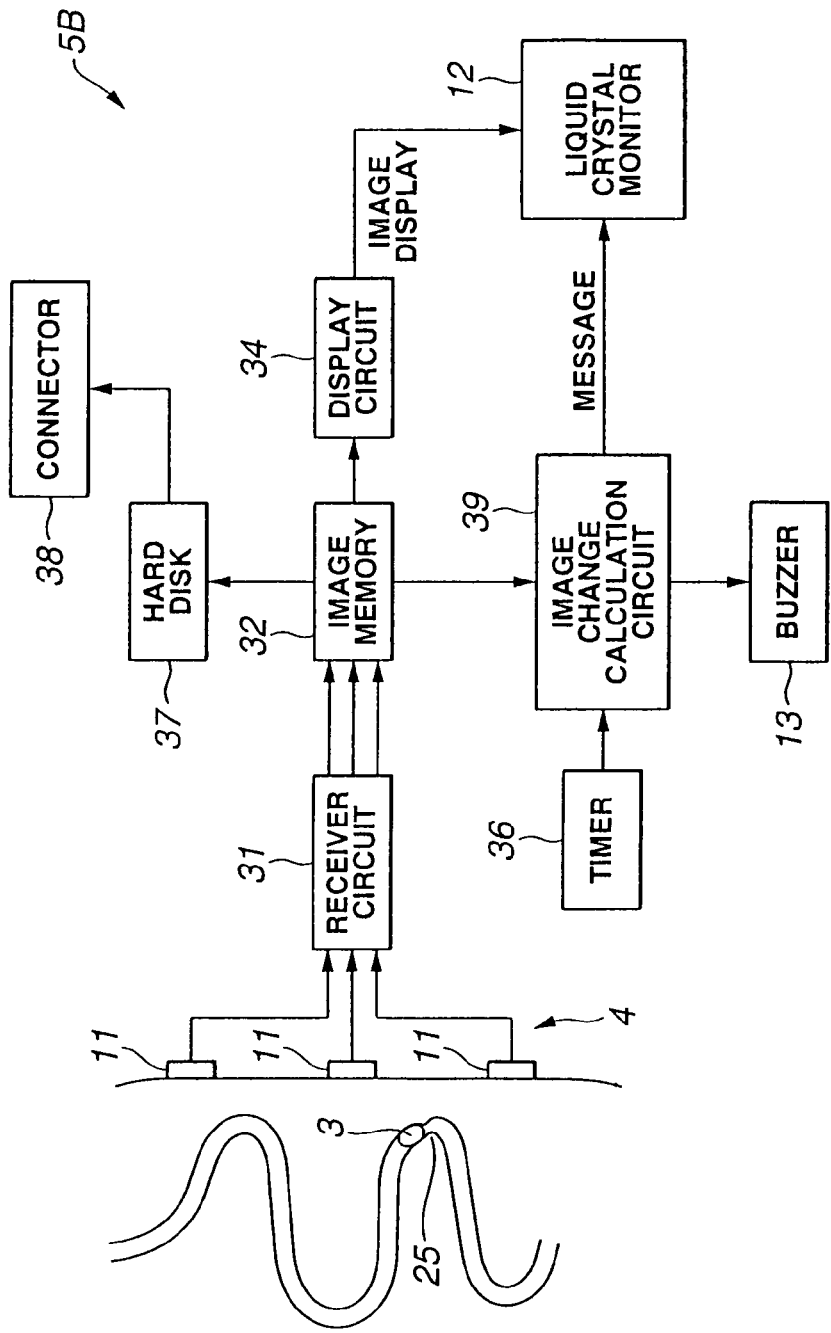

FIG. 6 shows the configuration of an extracorporeal unit 5B employed in a variant. The extracorporeal unit 5B shown in FIG. 6 is different from the extracorporeal unit shown in FIG. 3 in a point that image data stored in the image memory 32 is transferred to an image change calculation circuit 39. The image change calculation circuit 39 is connected to the timer circuit 36, and judges from a degree of agreement of images data items acquired at time instants separated by a predetermined time whether the position of the capsulated endoscope 3 has changed or the capsulated endoscope 3 has halted. If it is judged that the capsulated endoscope 3 has halted, the fact is notified.

The other components are identical to those shown in FIG. 3.

Operations to be exerted by the extracorporeal unit 5B shown in FIG. 6 will be described in conjunction with the flowchart of FIG. 7. According to FIG. 7, similarly to FIG. 5, an image is received through the plurality of antennas 11 at step S11. At step S12, image data is stored in the image memory 32. Image data provided as a signal of the largest strength among all image data items stored in the image memory is sequentially transferred to the hard disk 37.

At the next step S13, the image change calculation circuit 39 fetches the latest image stored in the image memory 32 and an image stored little earlier in the hard disk 37, for example, the latest image and an image acquired 5 sec previously. The image change calculation circuit 39 then superposes the latest image on the previous image.

At the next step S14, the image change calculation circuit 39 calculates a degree of agreement of the latest image with the previous image. For example, the absolute value of a difference between the levels of signals representing corresponding pixels of the images superposed on each other is integrated time-sequentially. Thus, the degree of agreement of one image with another can be calculated.

At the next step S15, the image change calculation circuit 39 judges whether the degree of agreement is equal to or larger than a threshold, for example, 80%.

If it is judged that the degree of agreement is smaller than 80%, it is judged that the capsulated endoscope 3 is moving. Control is then returned to step S11. The processing from step S11 to step S15 is repeated. In constant, if it is judged at step S15 that the degree of agreement is equal to or larger than 80%, it is judged at step S16 whether the degree of agreement equal to or larger than 80% has been detected ten consecutive times.

If it is judged that the degree of agreement equal to or larger than 80% has been detected less than ten times, it is judged that the endoscope has not halted. Control is then returned to step S11. In contrast, if the degree of agreement equal to or larger than 80% has been detected ten consecutive times, it is judged at step S17 that the endoscope has halted. At step S18, a warning message is displayed on the liquid crystal monitor 12 and the buzzer 13 is sounded for notification.

Moreover, in the capsulated endoscope 3 included in the present embodiment, if the batteries 21 incorporated in the capsulated endoscope 3 cause, for example, a fluid leakage 40, the fluid leakage 40 can be discerned through the transparent armor member 14 and transparent cylindrical member 22. Therefore, it can be avoided that the capsulated endoscope 3 is gulped down.

The related arts have a drawback that if a fluid leakage, moisture invasion, or the like occurs within a capsulated endoscope, unless the capsulated endoscope is disassembled, the fact cannot be verified. Therefore, an object of the present invention has been determined to make it possible to discern the fluid leakage, moisture invasion, or the like by externally looking at a main unit of a capsulated medical system such as the capsulated endoscope without the necessity of disassembling the capsulated endoscope. The present invention has accomplished the object.

Figure 9:
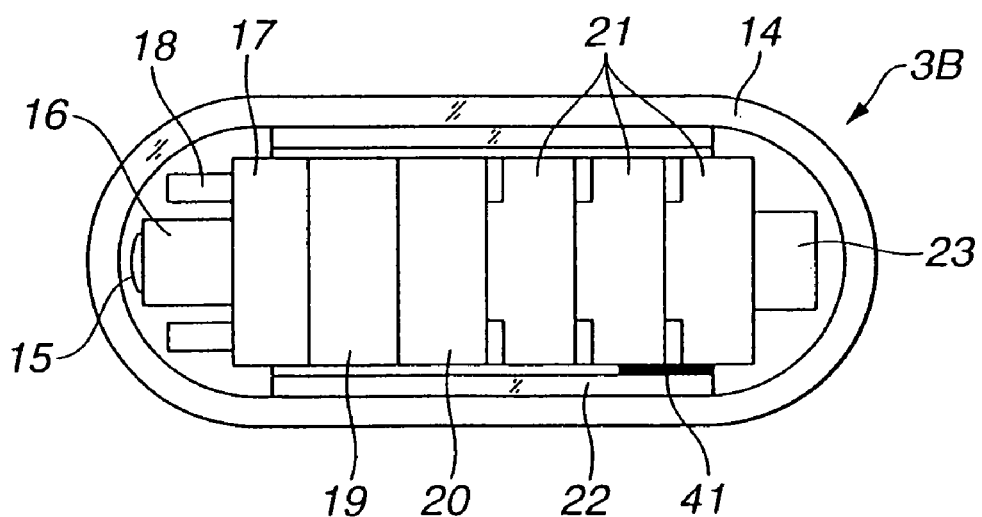

Unlike the capsulated endoscope 3, like a capsulated endoscope 3B employed in a variant, a means that changes its colors when sensing a fluid leakage or the like caused by the batteries 22 and that thus informs a patient or the like of the fact, for example, litmus paper 41 may be, as shown in FIG. 9, placed inside the transparent cylindrical member 22.

Incidentally, the cylindrical member 22 may not be employed. Instead, the litmus paper 41 or any other means that chemically reacts on a fluid leaking out of the batteries 22 to change its colors and whose color change can be readily discerned from outside may be placed inside the transparent armor member 14.

Second Embodiment

Figure 10:
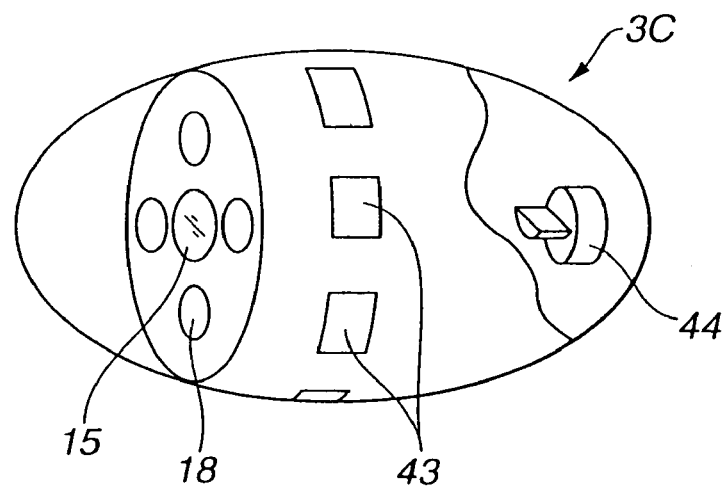
FIG. 10 to FIG. 12 are concerned with the second embodiment of the present invention.
Figure 11:
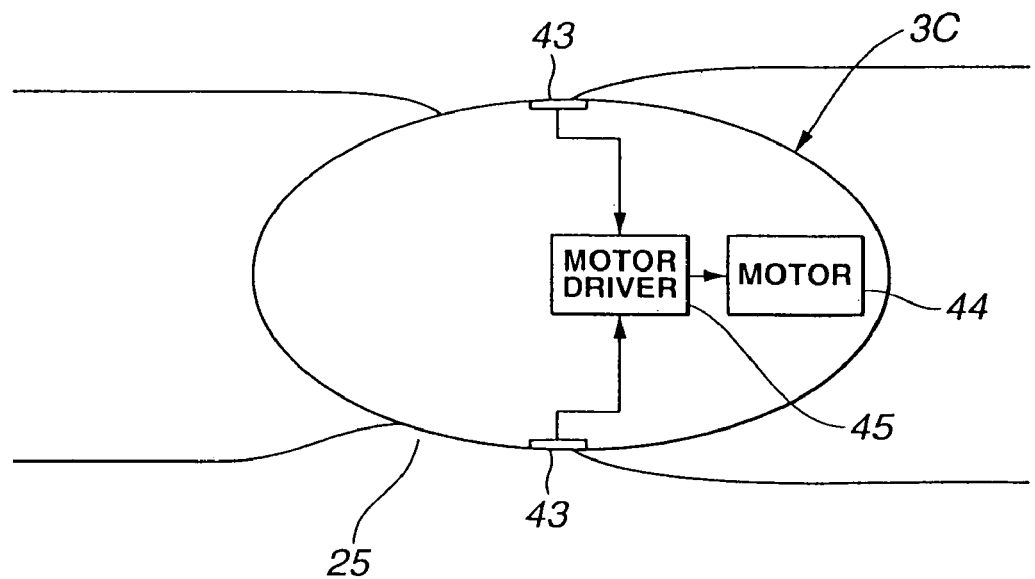
Figure 12:
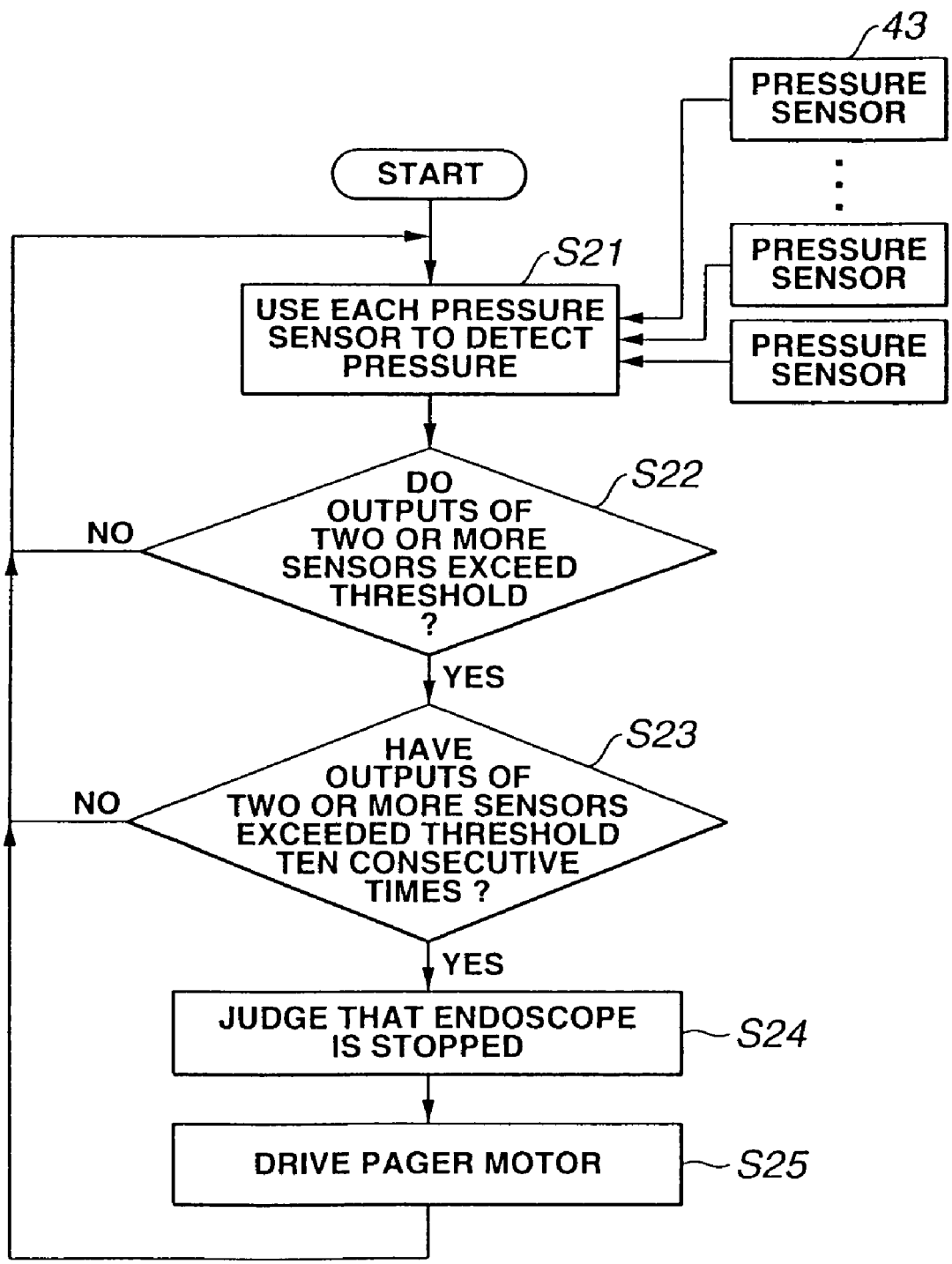

Next, the second embodiment of the present invention will be described with reference to FIG. 10 to FIG. 12. An object of the present embodiment is to provide capsulated medical equipment having a feature of detecting clogging of a capsulated body (a capsulated endoscope 3C in the present embodiment) in an early stage, and of automatically unclogging the capsulated body. FIG. 10 shows the capsulated endoscope 3C employed in the second embodiment.

The capsulated endoscope 3C is different from the capsulated endoscope 3 employed in the first embodiment in a point that the capsulated endoscope 3C has a plurality of pressure sensors 43 located on the periphery of a portion thereof having the largest diameter. Moreover, (a stator) of a pager motor (vibrating motor) 44 that is compact and vibrates is locked in the capsulated endoscope at the opposite end of the capsulated endoscope relative to the objective 15. The motor 44 is driven by a motor driver 45 as shown in FIG. 11.

The pager motor 44 is produced by attaching a member, of which center of gravity is made eccentric as if it were a cylinder having part thereof cut off, to the axis of rotation of an ordinary motor. When the pager motor is rotated, the motor 44 entirely vibrates because the center of gravity is eccentric to the axis of rotation. This causes the capsulated endoscope 3C, in which the pager motor is locked, to vibrate.

Moreover, the motor driver 45 receives pressure signals sent from the pressure sensors 43. When any of the pressure signals assumes a level equal to or higher than a set level (threshold in FIG. 12), the motor driver 45 drives the motor 44. Namely, the motor driver 45 not only has the ability to drive the motor 44 but also has the ability to judge whether the level of the pressure signal sent from any of the pressure sensors 43 is equal to or higher than the set value.

The other components are almost identical to those of the first embodiment. (For brevity's sake, FIG. 10 and FIG. 11 show only the major components of the present embodiment.)

According to the first embodiment, the extracorporeal unit 5 detects whether the capsulated endoscope 3 that is a capsulated body has halted for a certain period of time (however, a signal used for detection is sent from the capsulated endoscope 3). According to the present embodiment, the capsulated endoscope 3C itself has the detecting ability.

Next, operations to be exerted by the present embodiment will be described with reference to the flowchart of FIG. 12.

When the capsulated endoscope 3C starts acting, imaging is performed. At step S21, the pressure sensors 43 detect a pressure. Signals representing detected pressure values are transferred to the motor driver 45. The motor driver 45 fetches the signals, which represent the detected pressure values, one by one at intervals of, for example, 5 sec.

At step S22, the motor driver 45 judges whether outputs of two or more sensors exceed a pre-set threshold. If it is judged that the outputs of two or more sensors do not exceed the threshold, it is judged that the endoscope has not been clogged to halt. Control is then returned to step S21.

In contrast, if the outputs of two or more sensors exceed the threshold, control is passed to step S23. The motor driver 45 judges whether the outputs of two or more sensors exceeding the threshold have been detected ten consecutive times. If the outputs of two or more sensors exceeding the threshold have been detected less than nine times, control is returned to step S21.

In contrast, if it is judged that the outputs of two or more sensors exceeding the threshold have been detected ten consecutive times, the motor driver 45 judges that the capsulated endoscope 3C has halted at the stenosed region 25 and that pressure has been imposed on the capsulated endoscope as shown in step S23.

At step S25, the pager motor 44 is driven. The capsulated endoscope 3C vibrates when the pager motor 44 is driven. Consequently, the capsulated endoscope 3C may be unclogged from the stenosed region 25. Thereafter, control is returned to step S21.

After the completion of step S25, the number of times by which the pager motor 44 is repeatedly driven is measured. If the number of times becomes equal to or larger than a set value, the fact that the endoscope has halted may be informed outside.

According to the present embodiment, when the capsulated endoscope has halted, the pager motor 44 is driven. Even when the capsulated endoscope has halted at the stenosed region 25, if the capsulated endoscope 3C is vibrated, the capsulated endoscope 3C can be often unclogged from the stenosed region 25.

According to the present embodiment, the outputs of the pressure sensors 43 are transferred to the motor driver 45. The action of the pager motor 44 is controlled based on the outputs of the plurality of pressure sensors 43. This constituent feature of the present embodiment may be combined with that of the first embodiment.

To be more specific, the pager motor 44 and motor driver 45 are incorporated in the capsulated endoscope employed in the first embodiment.

As for the actions of the capsulated endoscope, an action of actuating the pager motor 44 is added as a step succeeding step S6 in FIG. 5. After the pager motor 44 is actuated, the position change calculation circuit 35 detects a change in the position of the capsulated endoscope. If a change in the position is detected, control is returned to step S1. If no change in the position is detected, control is passed to step S7. A warning may then be given.

In this case, if the capsulated endoscope can be unclogged to pass the stenosed region 25 owing to the action of the pager motor 44, it becomes unnecessary to collect the capsulated endoscope because of the stenosed region 25.

Figure 7:
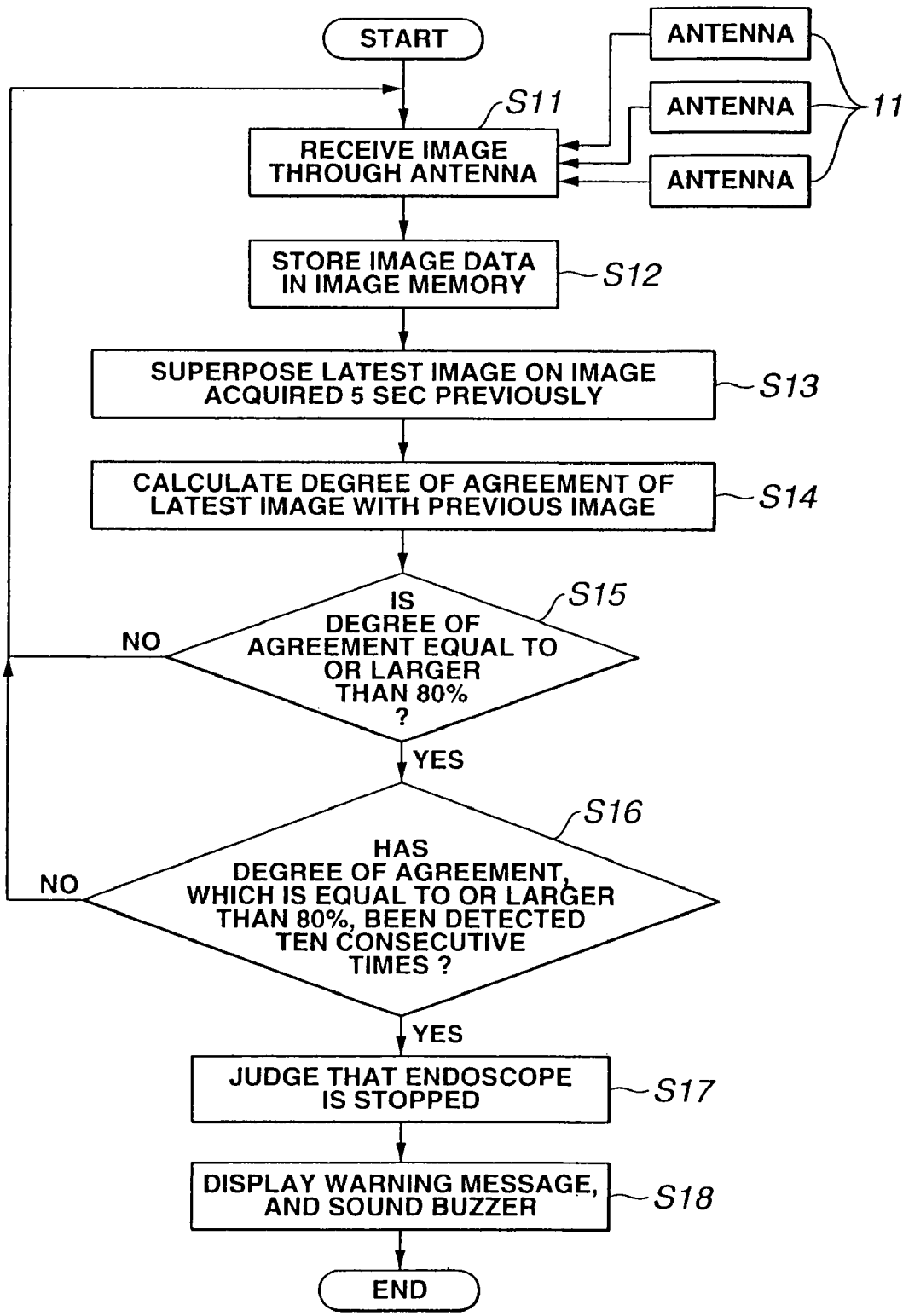
Figure 8:
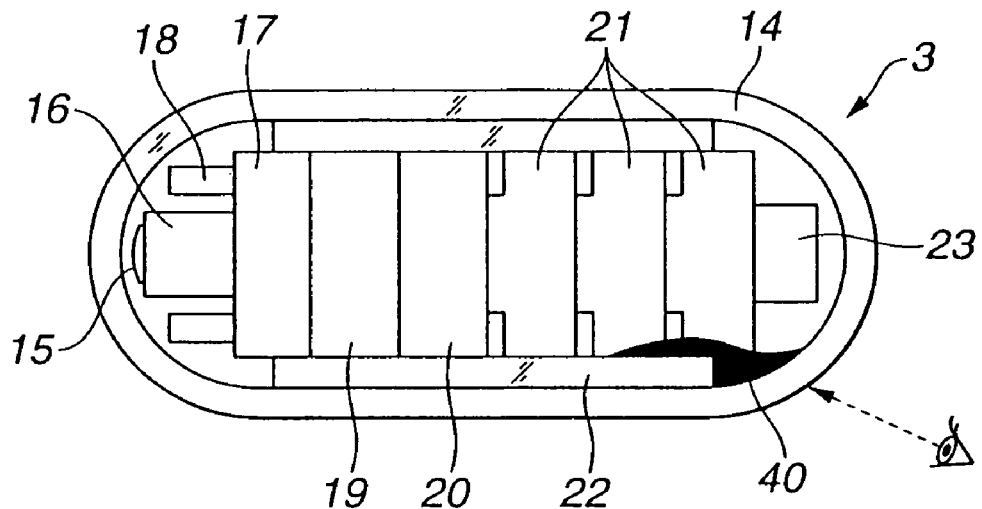

Moreover, when the capsulated endoscope is combined with the extracorporeal unit 5B shown in FIG. 6, an action of actuating the pager motor 44 may be added as a step succeeding step S17 in FIG. 7.

Third Embodiment

Next, the third embodiment of the present invention will be described with reference to FIG. 13 and FIG. 14.

Figure 13:
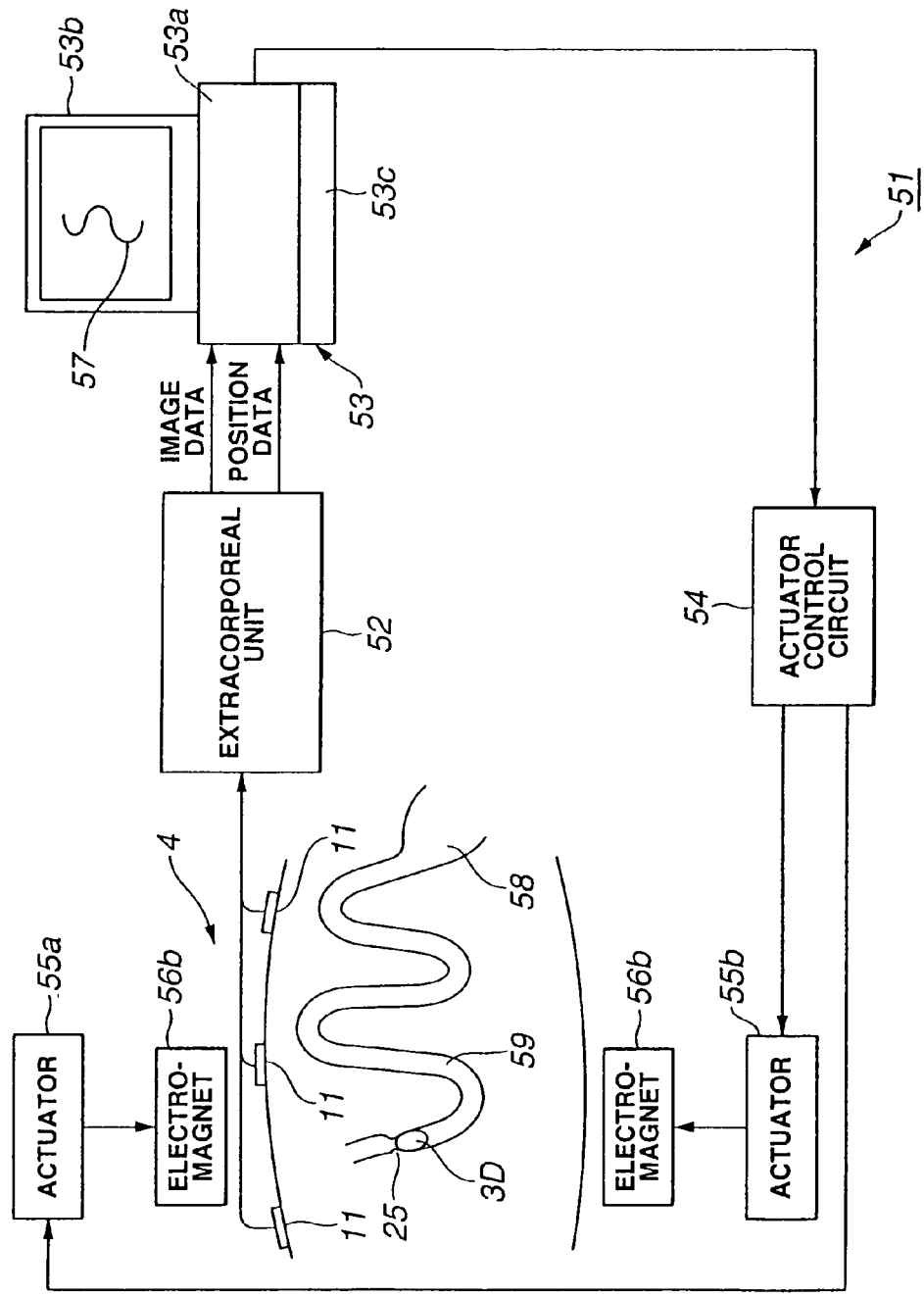

FIG. 13 shows a capsulated endoscope system 51 in accordance with the third embodiment. The system 51 consists mainly of a capsulated endoscope 3D, an extracorporeal unit 52, a personal computer 53, an actuator control circuit 54, actuators 55a and 55b, and electromagnets 56a and 56b. The extracorporeal unit 52 preserves image data produced by the capsulated endoscope 3D and calculates the position of the capsulated endoscope 3D. The personal computer 53 is connected to the extracorporeal unit 52. The actuator control circuit 54 is connected to the personal computer 53. The actuators 55a and 55b are driven with a driving signal sent from the actuator control circuit 54. The electromagnets 56a and 56b are three-dimensionally moved with thrusts produced by the actuators 55a and 55b respectively.

Figure 14A:
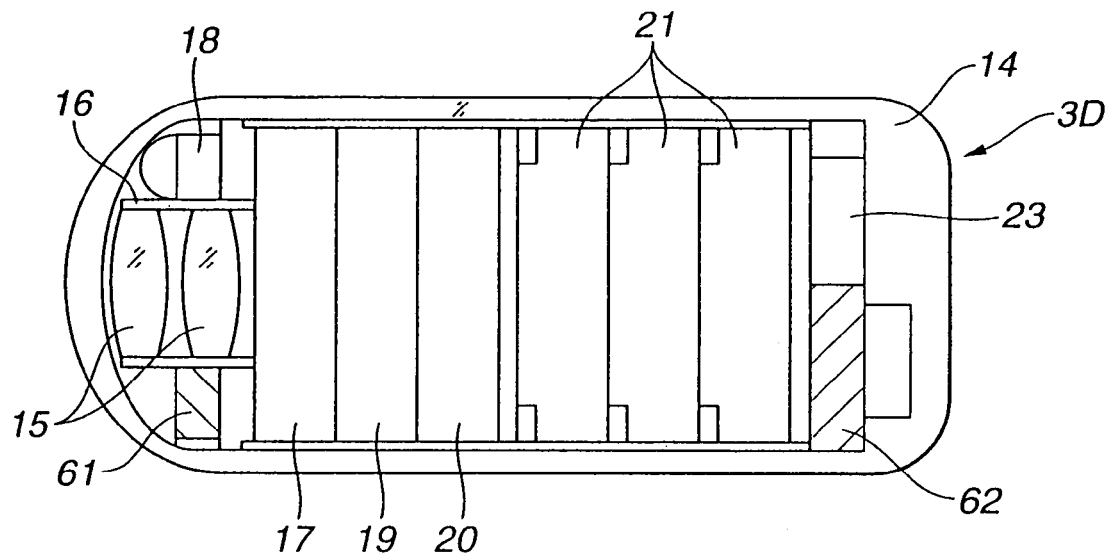
Figure 14B:
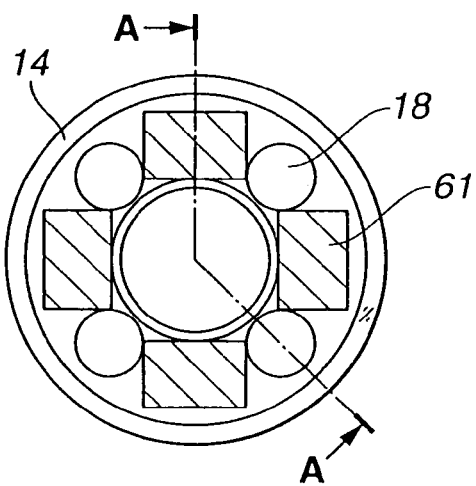
Figure 14C:
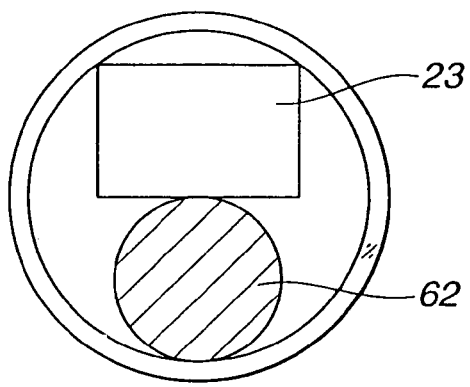

The capsulated endoscope 3D has the components thereof arranged as shown in FIG. 14A to FIG. 14C. Incidentally, FIG. 14A is a sectional view showing the components on A-A planes shown in FIG. 14B.

The capsulated endoscope 3D is different from the capsulated endoscope 3 shown in FIG. 2 in a point that permanent magnets 61 and 62 are placed at the front and rear end portions thereof. The permanent magnets 61 that are made of a rare earth element or compound such as neodymium or samarium cobalt and that produce large magnetic forces are arranged among a plurality of white LEDs 18 locked in the front end portion. The permanent magnet 62 is locked adjacently to the antenna 23 in the rear end portion.

As shown in FIG. 13, when the electromagnets 56a and 56b are externally: three-dimensionally approached to the capsulated endoscope 3D, the capsulated endoscope 3D can be moved three-dimensionally owing to the magnetic forces.

Moreover, the extracorporeal unit 52 is different from, for example, the extracorporeal unit 5 shown in FIG. 3 in a point that position data produced by the position calculation circuit 33 and image data stored in the image memory 32 can be transferred to the personal computer 53 (for example, the extracorporeal unit 52 includes dedicated connectors).

As shown in FIG. 13, with the extracorporeal unit 52 connected to a body 53a of the personal computer 53, image data preserved in the extracorporeal unit 52 and position data indicating a position at which the capsulated endoscope has picked up the image represented by the image data are transferred to the personal computer body 53a. The image data is stored in association with the position data in the hard disk incorporated in the personal computer body 53a. In this case, data representing a time instant is also stored in association with the image data.

When, for example, a keyboard 53c is used to enter an instruction that a trajectory should be displayed, a CPU incorporated in the body 53a reads position data items, which represent positions at which the capsulated endoscope 3D has picked up an image, in time-passing order. Based on the position data, a trajectory along which the capsulated endoscope 3D has moved is three-dimensionally depicted. The trajectory 57 along which the capsulated endoscope 3D has moved may be displayed on a monitor 53b.

Moreover, when the keyboard 53c is used to enter an instruction that the capsulated endoscope 3D should trace the trajectory 57, the personal computer 53 controls the actuator control circuit 54 to control driving of the actuators 55a and 55b and driving of the electromagnets 56a and 56b. Thus, the capsulated endoscope 3D can be guided to trace the trajectory 57 as instructed by utilizing magnetic forces.

Operations to be exerted by the present embodiment will be described in relation to a case where the capsulated endoscope 3D is, as shown in FIG. 13, used to examine an intracorporeal region.

The capsulated endoscope 3D gulped down through the patient's mouth passes through the esophagus and the stomach 58 and moves to the small intestine 59. In the meantime, an image picked up by the capsulated endoscope 3D is modulated and radiated in the form of a radio wave through the antenna 22. The radio wave is received by the extracorporeal unit 52 through the antennas 11 constituting the antenna unit 4.

In the extracorppreal unit 52, image data modulated by the receiver circuit 31 is stored in the image memory 32, and the position calculation circuit 33 calculates the position of the capsulated endoscope. The image data and position data are also transferred to the personal computer 53.

In the personal computer 53, the image data and position data (and time instant data) are preserved in the hard disk. For example, when the keyboard 53c is used to enter an instruction that a trajectory should be displayed, the trajectory 57 is three-dimensionally displayed on the monitor 53b using software, which displays a trajectory three-dimensionally, according to the position data concerning the capsulated endoscope 3D.

Moreover, as described in relation to the first embodiment, the extracorporeal unit 52 receives image data produced by the capsulated endoscope 3D through the plurality of antennas 11, and calculates a change in the position of the capsulated endoscope. When the capsulated endoscope 3D halts at the stenosed region 25 in, for example, the small intestine 59 and stops advancing, a message is displayed on the liquid crystal monitor 12. Moreover, the buzzer 13 is sounded in order to notify a user of the fact.

In this state, an endoscopic laboratory staff member uses the keyboard 53c to enter an instruction that the capsulated endoscope 3D should trace the trajectory 57. Consequently, the personal computer 53 controls the actuator control circuit 54 so that the electromagnets 56a and 56b held at the tips of the actuators 55a and 55b will be moved three-dimensionally in order to cause the capsulated endoscope 3D to trace the trajectory 57. Moreover, the magnitudes of magnetic forces exerted by the electromagnets 56a and 56b, and a direction of excitation are controlled so that the capsulated endoscope 3D interposed between the electromagnets 56a and 56b will be guided to trace the trajectory.

When the capsulated endoscope 3D is guided to, for example, the stomach 58, an endoscope that is not shown is inserted in order to collect the capsulated endoscope 3D.

According to the present embodiment, similarly to the first embodiment, whether the capsulated endoscope 3D has halted can be detected immediately. If the capsulated endoscope 3D has halted, magnetic forces are exerted in order to guide the capsulated endoscope 3D to a region in which the capsulated endoscope can be collected easily.

The present embodiment has been described on the assumption that the capsulated endoscope having halted at the stenosed region 25 is magnetically guided and then collected. Alternatively, the magnetic guidance may be utilized in order to, for example, facilitate movement.

Moreover, when the capsulated endoscope halts at the stenosed region 25, magnetic forces may be acted in a direction in which the capsulated endoscope is moved in order to pass the stenosed region 25. If the capsulated endoscope fails to pass the stenosed region 25, the capsulated endoscope may be traced in a direction in which it is moved in order to be collected.

Moreover, when the capsulated endoscope 3D has halted, an endoscope that is not shown is inserted into, for example, the stomach 58. An elongated collection tube lying through a channel within the endoscope is projected farther. A magnet may be attached to the tip of the collection tube and approached to the capsulated endoscope 3D, whereby the capsulated endoscope 3D attracted with magnetic forces may be manually guided to the stomach 58.

Fourth Embodiment

Figure 15:
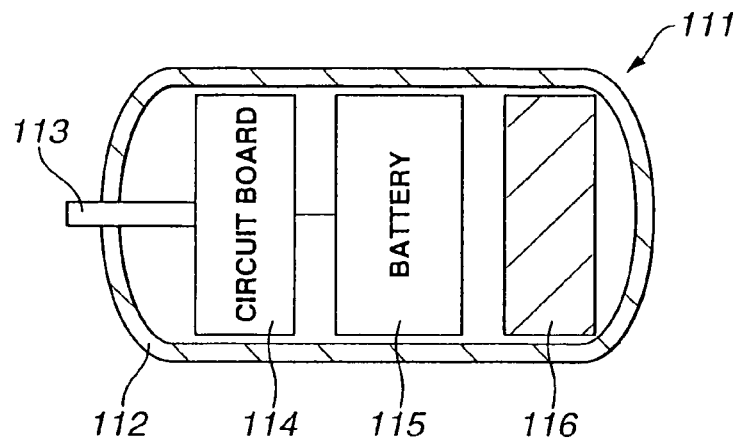
FIG. 15 to FIG. 17 are concerned with the fourth embodiment of the present invention.

Next, the fourth embodiment of the present invention will be described with reference to FIG. 15. FIG. 15 shows a main unit 111 of a capsulated medical system in accordance with the fourth embodiment of the present invention.

The main unit 111 of the capsulated medical system has a capsulated body 112 kept watertight and composed of a cylindrical part and covers that cover both the end portions of the cylindrical part. A detector, for example, a pH sensor 113 for detecting a pH value is adopted as a means for detecting biomedical information concerning an intracavitary region, and projected (or exposed) from one of the end portions.

When the detector that is the pH sensor 113 is designed to jut out of a hole bored in the capsulated body 112, the detector is fixed using an adhesive that exerts a great effect of watertightness. Thus, the capsulated endoscope is kept watertight.

The rear end of the pH sensor 113 is connected to a circuit board 114 lying within the capsulated body 112. The circuit board 114 accommodates a means for detecting a pH value, a means in which pH data is stored, a communicating means that transmits pH data to an extracorporeal unit located outside, and an antenna. Moreover, the circuit board 114 is connected to a battery 115 that supplies power with which the circuit board 114 is activated.

Moreover, according to the present embodiment, a permanent magnet (or a ferromagnetic substance) 116 is placed near the end portion of the capsulated body 112 opposite to the end portion thereof in which the pH sensor 113 is placed, so that the main unit 111 can be collected readily by utilizing magnetic forces.

An extracorporeal unit included in the capsulated medical system in accordance with the present embodiment is different from the extracorporeal unit 5 included in the first embodiment in a point that a signal demodulated by the receiver circuit 31 is transferred to a pH memory but not to the image memory 32, and preserved in the pH memory.

As described in relation to, for example, the first embodiment, if it is judged that the main unit has halted, if a warning is given, the main unit can be moved to a region in which the main unit can be readily collected using a magnetically guiding assembly shown in FIG. 13.

According to the present embodiment, the pH sensor 113 for detecting a pH value is adopted as a biomedical information examining means for acquiring biomedical information that is used for medical purpose. Alternatively, a temperature sensor, a pressure sensor, a light sensor, or a blood sensor (more particularly, a hemoglobin detection sensor) may be adopted.

According to the present embodiment, the sensor (detector) acquires information such as a chemical quantity (pH value) concerning an intracorporeal fluid, temperature of each organ, pressure imposed on the outer surface of a capsulated body by the inner surface of a lumen through which the capsulated body passes, brightness in a living body, or an amount of hemoglobin in each organ (bleeding or not). The information is temporarily stored in a memory, which is not shown, incorporated in the capsulated body. Thereafter, a communicating means that is not shown transmits the data to a receiving means incorporated in an extracorporeal unit placed outside.

Consequently, the acquired data received by the receiving means is compared with a reference value. Thus, a physician, co-medical, or paramedic can judge in vitro whether an illness, bleeding, or any abnormality is found, or can identify a position through which a capsule has passed or a state in which the capsule has passed.

In particular, the capsulated medical system makes it possible to measure a pH value in the alimentary track of a living body or an amount of hemoglobin without giving a subject any pain. This is quite advantageous in terms of assessment or physiological analysis of a disease of an alimentary organ. If a plurality of types of sensors is included based on a purpose of use, examination can be achieved efficiently.

Figure 16:
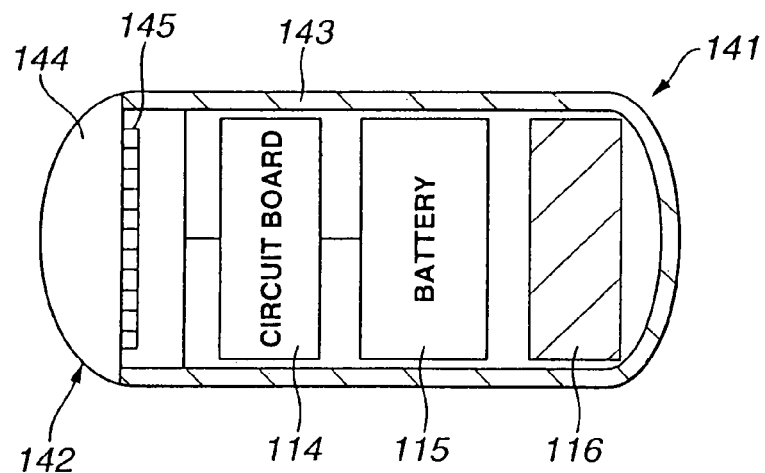

The main unit 111 of the capsulated medical system including various sensors has been described in conjunction with FIG. 15. An ultrasonic probe 142 for use in producing an ultrasonic image may be, as shown in FIG. 16, included on behalf of the various sensors, whereby a main unit 141 of a capsulated medical system may be realized.

In the main unit 141 of the capsulated medical system, an acoustic lens 144 serving as the face of the ultrasonic probe 142 is formed on the face of a capsulated body 143 so that the acoustic lens 144 will be exposed on the outer surface of the capsulated body 143. The acoustic lens 144 is secured to the capsulated body 143 using an adhesive in order to keep the capsulated body watertight. Thus, the capsulated body 143 is kept watertight.

Numerous ultrasonic transducer elements 145 required for electronic scanning are arranged on the inner surface of the acoustic lens 144 included in the ultrasonic probe 142. A circuit board 114 is located behind the acoustic lens. The circuit board accommodates an ultrasound transmitting/receiving circuit for transmitting or receiving ultrasonic waves and a circuit for producing an ultrasonic tomographic image using a signal sent from the ultrasound transmitting/receiving circuit. The circuit board 114 is driven with power supplied from a battery 115. Moreover, a permanent magnet 116 is placed in the rear end portion of the main unit 141.

In the main unit 141 of the capsulated medical system, the ultrasound transmitting/receiving circuit accommodated by the circuit board 114 produces an ultrasonic tomographic image of an intracavitary region. Similarly to the first embodiment, acquired data is transmitted to an extracorporeal unit. This enables assessment of the presence or absence of an abnormality in a direction of depth in a deep portion of a body cavity, such as, the small intestine.

An optical observation means (imaging means) may also be included. In this case, the superficial region and deep region of a body cavity can be diagnosed at a time.

Figure 17:
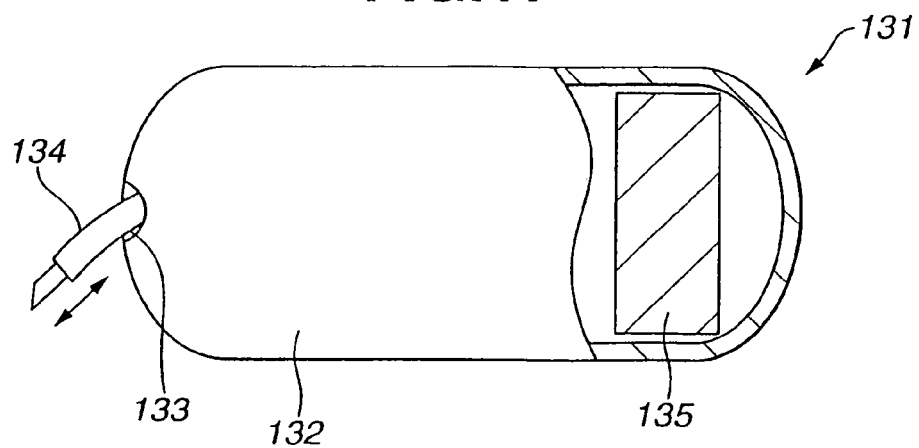

FIG. 17 shows a main unit 131 of a capsulated medical system in accordance with the second variant.

The main unit 131 of the capsulated medical system has a capsulated body 132 composed of a cylinder portion and covers that cover both the ends of the cylinder portion in an arc. An opening 133 is bored in one of the end portions of the capsulated body 132 so that, for example, an injector 134 to be used to administer a medicine can be freely thrust or sunk through the opening. A driving means for causing the medicine administration injector 134 to thrust or sink and a control means for controlling the driving means are incorporated in the capsulated body 132. In response to a control signal sent from outside, the medicine administration injector 134 is thrust or sunk in order to administer a medicine. Moreover, a signal of certain strength is delivered from an antenna incorporated in the main unit 131 to an extracorporeal unit located outside so that the position of the main unit 131 of the capsulated medical system can be calculated.

A permanent magnet or a ferromagnetic substance 135 is placed near the end opposite to the end of the capsulated body 132 at which the opening 133 is bored.

A blood sensor or an observation means is used to identify a bleeding region. Thereafter, a treatment appliance such as an injector that is used to administer a hemostatic agent and placed in the capsulated body is instructed to move through communication with an external device. Thus, ethanol that is a hemostatic agent or a powdered chemical can be sprayed to the bleeding region in order to arrest bleeding.

According to the present variant, hemostasis or any other treatment can carried out.

The present variant may be adapted to a capsulated medical system for spraying a medical solution into a living body or collecting a humor.

Incidentally, an embodiment constructed by combining parts of the aforesaid embodiments will belong to the present invention.

The preferred embodiments of the present invention have been described with reference to the accompanying drawings so far. It will be understood that the present invention is not limited to the embodiments but that a person skilled in the art can make various changes or modifications without a departure from the spirit or scope of the invention defined in the appended claims.

What is claimed is:

1. A capsulated medical equipment comprising:
   a capsulated body, an entire armor case of which is inserted into a living body and passed through a duct in the living body;
   a driving unit provided in the capsulated body, for causing a needle to thrust outside and sink inside the capsulated body;
   a control unit provided in the capsulated body, for controlling the driving unit;
   a position detection unit provided outside the capsulated body, for detecting the position of the capsulated body;
   a judgment unit for judging whether or not the capsulated body is in a halted state where the capsulated body has halted in the duct for a certain period of time, based on position information concerning the capsulated body provided by the position detection unit;
   a trajectory arithmetic unit for performing arithmetic operations to calculate a trajectory, along which the capsulated body has moved, using the position information concerning the capsulated body provided by the position detection unit;
   a magnet or magnetic substance that is incorporated in the capsulated body and that reacts on magnetic forces; and
   a guiding assembly for guiding the capsulated body to move from outside the living body by utilizing the magnetic forces,
   wherein when the judgment unit judges that the capsulated body is in the halted state where the capsulated body has halted for a certain period of time in the duct, the halted state is notified and the capsulated body is guided in a direction opposite to the trajectory using the guiding assembly.

2. The capsulated medical equipment according to claim 1, wherein the needle is an injector.

3. The capsulated medical equipment according to claim 2, wherein a hemostatic agent is injected in a bleeding region by the injector.

4. The capsulated medical equipment according to claim 3, wherein the hemostatic agent is ethanol.

5. The capsulated medical equipment according to claim 1, wherein the trajectory of the capsulated body calculated by the trajectory arithmetic unit is displayed on a display device.

6. The capsulated medical equipment according to claim 1, wherein the capsulated body includes a blood sensor or an observation device for detecting a bleeding region.

7. The capsulated medical equipment according to claim 6, wherein information acquired by the blood sensor or the observation device is transmitted by radio to an extracorporeal unit placed outside the living body.

* * * * *